United States Patent [19]

Lenz et al.

[11] Patent Number: 4,914,040
[45] Date of Patent: Apr. 3, 1990

[54] REAGENT AND METHOD FOR DETERMINATION OF A POLYVALENT SUBSTANCE USING AN IMMUNOAGGREGATE

[75] Inventors: Helmut Lenz; Ellen Mössner, both of Tutzing; Werner Stock, Gräfelfing; Albert Röder, Seeshaupt; Harald Haug, Peissenberg, all of Fed. Rep. of Germany; Robert C. McCarthy, Carmel, Ind.

[73] Assignee: Boehringer Mannheim GmbH, Mannheim, Fed. Rep. of Germany

[21] Appl. No.: 164,054

[22] Filed: Mar. 3, 1988

[51] Int. Cl.$^4$ ............... C01N 1/00; C01N 33/503; C01N 33/53
[52] U.S. Cl. ................... 436/175; 431/512; 431/824; 431/825; 431/548
[58] Field of Search ............... 436/512, 824, 825, 548, 436/531, 175

[56] References Cited

U.S. PATENT DOCUMENTS

| | | | |
|---|---|---|---|
| 4,474,892 | 10/1984 | Murad | 436/519 X |
| 4,569,919 | 2/1986 | Toth | 436/531 X |
| 4,582,810 | 4/1986 | Rosenstein | 436/528 |
| 4,624,930 | 11/1986 | Tanswell | 436/512 X |
| 4,659,678 | 4/1987 | Forrest | 436/548 X |
| 4,680,274 | 7/1987 | Sakai | 436/825 X |

OTHER PUBLICATIONS

Sevier et al., "Monoclonal Antibodies in Clinical Immunology", Clin. Chem., 27 (1981), 1797–1806.

Primary Examiner—Robert J. Hill, Jr.
Assistant Examiner—Karen J. Krupen
Attorney, Agent, or Firm—Felfe & Lynch

[57] ABSTRACT

The invention teaches a method for improving the ability to determine a polyvalent substance via use of an immunoaggregate during the assay. The immunoaggregate eliminates substances which can lead to incorrect results otherwise.

41 Claims, 2 Drawing Sheets

Fig. 2.

REAGENT AND METHOD FOR DETERMINATION OF A POLYVALENT SUBSTANCE USING AN IMMUNOAGGREGATE

The invention relates to an improved method for the determination of a polyvalent component, capable of bonding immunologically, in the presence of at least two immunoreactants, specific for the component capable of binding immunologically, and in the presence of an inhibitor to compensate for interfering factors in human serum samples, as well as a reagent suitable for this.

The sensitive determination of components, capable of binding immunologically, such as polyvalent antigens (peptides, proteins, polysaccharides, viruses, bacteria, specific cells) using two or optionally more antibodies, which are directed against spatially different antigen determinants, is known as an immunoradiometric or immunoenzymometric sandwich assay (two-site immunoassay). The most common method for carrying out this known determination is one in which the antigen that is to be determined (sample) is incubated with a first antibody, which either is bound in solid phase to a suitable carrier material such as sepharose, agarose, plastic tubes, etc., or present homogeneously, for example, biotinylated, in solution, and a certain quantity of a second labeled antibody or of additional labeled antibodies in liquid phase. The specificity of the second antibody and of optionally additional antibodies preferably is selected so that the determinants of the antibody to be determined, against which they are directed, are different from those against which the first antibody is directed in order to exclude competition between the antibodies for the same bonding sites on the antigen that is to be determined. Such competition would interfere with the sensitivity of the test. The first labeled antibody, which is bound to the solid phase or, for example, biotinylated, as well as the second or additional labeled antibody present in solution are added in excess. The respective antigen can be determined from the activity, which is fixed to the first antibody, or from the activity, which remains in solution and is not bound immunologically. In the latter case, it is necessary to add a defined amount of the second, labeled antibody.

Because of the required specificities, complete IgGs, especially those derived from monoclonal antibodies (MABs), or their immunologically reactive fragments (Fab, F(ab')$_2$) are used for the immunological sandwich assays. It is, however, also possible to use immunoreactive components in these tests, which are derived from polyclonal antibodies (PABs).

Although specific antibodies are used in the two-site immunoassay described for the analytes that are to be determined, human serum samples frequently contain substances which lead to nonspecific reactions. This occurs with a significant frequency. These lead to wrong test results with correspondingly serious consequences for therapeutic measures. The occurrence of nonspecific reactions can be attributed to substances present in the sample, which, like the analytes to be determined (polyvalent antigen), bind to the specific immunoglobulin reagents. Generally, these interfering factors bind to the immunoreactant at a different site than the component being detected, but still lead to the formation of complexes even in the absence of analyte.

Usually therefore, nonspecific non-aggregated immunoglobulins or immunoglobulin fragments (generally immunoglobulin G, IgG) of the same animal species, from which the specific antibodies originate, are added preventively in excess to such immunoassays (G. M. Addison in Radioimmunoassay and Related Procedures in Medicine, vol. 1, 131–147 (1974); European Patent Application 0,174,026). The use of specific non-aggregated monoclonal antibodies, which usually originate from the mouse, however requires large amounts of nonspecific mouse IgG in the form of mouse serum, mouse ascites or isolated mouse immunoglobulin to achieve interference-suppression (approximately 300–500 $\mu$g/mL; Clin. Chem. 32: 1491–1495 (1986)). For example, according to the European Patent Application 0,174,026, complete compensation of the interference through the addition of, for example, 30 $\mu$g/mL of relevant, nonspecific mouse or rat IgG to immunoassays of the type described is achieved only in particular sera and in special cases (negative samples). However, the preparation of mouse IgG on the required kilogram scale is not possible with the presently available methods under economically interesting conditions and is critical from ethical points of view.

An essential measure to avoid interference in immunoassays of the aforementioned type is the use of Fab or F(ab')$_2$ fragments for at least one of the specific antibodies used in the immunoassay. With this, all interfering factors in the sample, which are directed to Fc portions of IgG (rheumatoid factors, anti-Fc immunoglobulins such as IgM), lose their point of attack on one of the specific immune reagents and thus need not be compensated for.

However, interferences continue to occur in some human sera in immunoassays despite the use of Fc-free specific antibody reagents. These are attributed to substances in the serum, which are directed to Fab or F(ab')$_2$. According to the European patent specification No. 0,083,869, such interfering factors recognize Fab regions, however only when these are separated from the Fc portion. These can be removed in appropriate immunoassays by the addition of native or aggregated Fab or F(ab')$_2$ fragments, which are not specific for antigen that is to be determined (EP-B 0,083,869). In this connection, aggregated Fab or F(ab')$_2$ fragments show a 2 to 3 times higher interference-suppressing effect than do native components. According to EP-B 0,083,869 on the other hand, completely nonspecific IgGs, in native as well as in aggregated form, bring about no interference-suppressing effect in said immunoassays. The method, moreover, has the significant disadvantage that, aside from the immunoglobulin reagents specific for the antigen that is to be determined, considerable amounts of highgrade, nonspecific immunoglobulin reagents are required. This entails significant economic as well as ethical problems. According to this method, for example, at least 100 $\mu$g/mL of the aggregated, nonspecific Fc-free immunoglobulin fragments, which have proven to be effective, are used to suppress the interference.

It is therefore an object of the invention to provide new possibilities for the compensation of nonspecific reactions in immunoassays with Fc-containing and Fc-free specific antibody reagents as specific reactants, by means of which interfering factors in human sera, which are directed to complete IgGs and to Fab or F(ab')$_2$ fragments, are reliably eliminated and which permit economic utilization of the improved test systems, while taking into consideration ethical points of view.

Pursuant to the invention, this objective is accomplished by a method for the determination of a component in a sample of a biological fluid of a first species in the presence of at least two immunoreactants of another animal species, which are specific for the component, and in the presence of an inhibitor that compensates for interfering factors in said sample wherein the reaction mixture is brought into contact with 0.1-50 μg/mL of an aggregate of antibody species different from said first species, which is not specific for the component that is incapable of binding immunologically and which are derived from monoclonal or polyclonal antibodies, to compensate for interfering factors, under conditions favoring formation of an identifiable complex between said component and said immunoreactants, and determining said complex or non-complexed immunoreactant as a measure of said component.

Examples of components which can be detected include polyvalent antigens, such as peptides, proteins, polysaccharides, viruses, bacteria and other specific cells or fragments thereof. As specific immunoreactants for the component to be determined, polyclonal as well as monoclonal antibodies can be used; preferably, IgGs and their immunoreactive components, such as Fab or F(ab')$_2$ fragments are used in combination. Especially preferred is the use of two or optionally several specific reactants, of which at least one is an Fab or an F(ab')$_2$ fragment and the remaining specific reactants are complete IgGs.

As antibody aggregates which are not specific for the component and which compensate for interferences, aggregates of IgGs which are not specific for the component are preferred. Especially preferred is an IgG aggregate comprising nonspecific IgG and a further macromolecule. Nonspecific IgGs are preferred which originate from the same animal species as at least one of the specific immunoreactants. Suitable macromolecules are, e.g., Fab or F(ab')$_2$ fragments, that is, Fc-free IgG fragments, which originate from the MABs or PABs derived from the mouse or some other species, as well as proteins (such as albumin), polysaccharides (such as dextran) or other water-soluble polymers (for example, appropriate latex particles).

Other IgG heteropolymers can be formed, e.g., from single molecules of mouse or bovine IgG. These heteropolymers can also be used to compensate for interference in samples being assayed. Especially preferred is the use of aggregates comprising an IgG molecule and an Fc-free IgG fragment, the IgGs as well as the Fc-free IgG fragments originating from the same species of animal as one of the specific immunoreactants. Such IgG/Fab or IgG/F(ab')$_2$ polymers exhibit an interference-suppressing action, which is even better than that of a pure IgG aggregates by a factor of about 3. For successful supression of interference concentrations of antibody aggregates ranging from about 0.1 to about 50 μg/mL are sufficient, depending on the individual serum sample. However concentrations of from about 5 to about 25 μg/mL and especially from about 5 to a maximum of about 10 μg/mL are preferably used, since a much smaller addition of nonspecific IgG aggregates is already fully effective in most cases.

In accordance with a preferred embodiment of the invention, nonspecific homopolymeric or heteropolymeric IgG aggregates or IgG/Fab or IgG/F(ab')$_2$ aggregates with molecular weights of about 320,000 daltons and higher, are used to compensate for interfering factors in human sera. Moreover, the IgG aggregates contain IgG of the species from which at least one of the specific immunoreactants originates, and preferably belong to the same subclass as at least one of the specific reactants. Preferably, polymeric IgG preparations are used with molecular weights of from about 320,000 to about 10 million daltons, the compensation effect relative to the serum interference factors growing with increasing molecular weight. Especially preferred embodiments of the invention are two-site immunoassays with two or more specific mouse or rat MAB immunoreactants, of which at least one reactant is an Fab or an F(ab')$_2$ fragment and at least one of the other reactants is an Fc-containing IgG, to which homopolymeric or heteropolymeric, nonspecific IgG aggregates or IgG/Fab or IgG/F(ab')$_2$ aggregates with molecular weights greater than 320,000 daltons are added to compensate for interfering factors, the IgGs and Fab or F(ab')$_2$ fragments contained in the nonspecific aggregates being monoclonal and from the same species and subclass as at least one of the specific reactants. In this connection, it is immaterial whether the nonspecific IgG or Fab fragment is produced from ascites fluids, fermentation, or by way of genetic engineering through expression in microorganisms or transgenic animals.

The polymerized, nonspecific IgG molecules as well as the nonspecific IgG/Fab or IgG/F(ab')$_2$ aggregates, which compensate for interference according to the invention, must be derived from a species other than that from which the sample to be analyzed originates. As a rule, immunological methods of determination are used for the analysis of human sera using specific antibodies or their immune fractions, which are derived from the mouse. The specific antibody reagents may, however, also originate from a different animal species. The nonspecific antibody aggregates, added to suppress the interference, may originate from the mouse or, in combination with mouse IgG or its Fab fragments, originate from another animal species, which differs from the first. For example, mouse IgG/bovine IgG heteropolymers, described supra can be used to suppress interference in immunoassays, which employ mouse MABs or mouse IgGs as specific antibody reagent.

Through the addition of nonspecific IgG aggregates or IgG/Fab or IgG/F(ab')$_2$ aggregates, nonspecific reactions are compensated for in immunoassays with at least two reactants specific for the component to be determined, at least one of which is derived from an Fab or F(ab')$_2$ fragment. The effectiveness of the compensation is increased by a factor of 20 to 1,000 relative to that of native IgGs, by a factor of 20 to 1,500 relative to that of native Fc-free IgG fragments and by a factor of 3 relative to that of aggregated Fc-free IgG fragments. This is surprising, since it could not have been anticipated that IgG-containing nonspecific reactants can bring about any compensation at all of interferences directed to Fab or F(ab')$_2$ fragments in immunoassays, in which Fc-free specific immunoglobulin reagents of monoclonal or polyclonal antibodies participate. Moreover, EP B 0,083,869, which is the state of the one of the art that comes closest to this invention, would, if anything, lead those skilled in the art to assume the opposite, because it is explicitly emphasized in this patent that native, as well as aggregated IgGs show no interference-suppressing effect in the immunological agglutination test cited there and that the reagents which are added for the suppression of interference and also for the specific agglutination, must be free of IgG.

The nonspecific IgGs can be cross linked with one another or with antibody fragments, as well as with proteins, polysaccharides or other water-soluble macromolecules by the action of heat or chemically by methods known from the literature. In each case, aggregates are formed which are soluble in aqueous buffer solutions. The chemical cross linking can be accomplished, for example, by homobifunctional and heterobifunctional chemical connecting arms (cross linkers), by way of proteins or activated dextran or by self-cross linking of the IgG molecules or their and/or other Fc-free fragments with carbodiimide. Moreover, it is possible to crosslink the antibody monomers with one another or with a suitable macromolecule through disulfide reduction and reoxidation or through oxidation of their carbohydrate portion. As chemical cross linkers, such compounds as bis(maleicimide) methyl ester dimethyl suberimidate, disuccinimidyl suberate, gluraric dialdehyde, N-succinimidyl-3-(2-pyridylthio)-propionate, N-5-azido-2-nitrobenzoylsuccinimide, N-succinimidyl(4-iodoacetyl)-aminobenzoate) or the combination of maleicimidohexanoylsuccinimidate and S-acetylmercaptosuccinic anhydride or similar compounds can be used. Activated dextran can be produced, for example, by reacting aminodextran of a defined molecular weight with maleicimidohexanoylsuccinimidate, which is subsequently cross linked with mercaptoacetyl-derivatized nonspecific IgG molecules. The crude mixtures obtained can be used directly after dialysis or separated, by gel filtration for example, into fractions with increasing molecular weight and subsequently used directly to compensate for interfering factors in immunoassays.

One of the specific reactants added to the test mixture, preferably the Fc-containing IgG antibody, is bound in a solid phase by methods known to those skilled in the art, to a carrier material, such as agarose or plastic tubes, etc. or is present linked to biotin for example, in liquid phase. If a biotinylated first antibody is used, the complex of antigen and a labeled second specific reactant is formed. This complex is then bound in situ to a protein, which forms a bond with biotin, such as a carrier material coated with avidin or streptavidin. The test can, however, also be conducted in other ways with a first biotinylated antibody. For example, the antigen is reacted with the biotinylated MAB and is bound in situ or after a certain pre-incubation period to a biotin binding solid phase and only then brought together with the second, specific reactant. It is also possible to react the antigen at first with the second specific reactant and subsequently with the biotinylated antibody. The labeling of the second reactant and optionally of further specific reactants, which preferably are Fc-free IgG fragments, is accomplished by coupling with an enzyme or a fluorescent, chemiluminescent or radioactive substance. Methods for labeling such antibody derivatives are known to those skilled in the art, for example, from Ishikawa, et al., J. of Immunoassay 4 (1983) 209-327, and require no further explanation here.

A further object of the invention are reagents and diagnostic means for determining polyvalent components capable of binding immunologically, in two-site immunoassay, which contain the described nonspecific antibody aggregates.

Aside from two or optionally more specific antibodies, one of which is an IgG molecule and at least one of which is an Fc-free IgG fragment, the reagents and diagnostic means contain a suitable buffer system and the described nonspecific antibody aggregates, and may contain other optional auxiliary substances such as reaction accelerators, detergents or stabilizers. As suitable buffer systems, 20 to 60 mM of phosphate buffer (pH 7.0) or a 50 mM HEPES/100 mM NaCl buffer system (pH 7.4) may, for example, be used. Materials such as dextran sulfate or polyethylene glycol, with a molecular weight of 6,000 to 40,000 can be used as reaction accelerators, materials such as Triton X 100, Tween 20 or pluronic F 68 as detergents and phenol, oxypyrion chloracetamide, merthiolate, etc. may be used as stabilizers.

The reagents and diagnostic means contain the nonspecific antibody aggregate with molecular weights of from about 320,000 daltons and higher, preferably up to about 10 million daltons at a concentration of 0.1 to 50 $\mu$g/mL, preferably of 5 to 25 $\mu$g/mL and especially of 5 to 10 $\mu$g/mL.

The reagents and diagnostic means may be present in the form of a solution or of a dry chemical reagent absorbed on an absorptive support or in an open film.

The diagnostic means of the invention, when in the form of a solution that optionally is buffered to the desired pH, preferably contains all reagents required for the test. For stability reasons, it may be advantageous to divide the reagents required for the test amount into two or more solutions, which are mixed only when the actual investigation is carried out. In this connection, it is immaterial whether the nonspecific antibody aggregates are added separately in a suitable buffer system and/or with one and/or two or more specific antibodies.

To produce the diagnostic means in the form of a test strip, an absorptive carrier, preferably filter paper, cellulose or a nonwoven plastic material is impregnated with solutions of the required reagents, which are normally used to produce test strips, in volatile solvents, such as water, methanol, ethanol or acetone. This may be accomplished in one impregnating step. Frequently however, it is advisable to carry out the impregnation in several steps, solutions being used, which in each case contain a portion of the components of the diagnostic means.

Furthermore, an open film can be used to produce the diagnostic means in the form of a test strip. Aside from the film-forming agents and pigments, this open film contains the specific antibodies or fragments, the described nonspecific antibody (fragment) aggregates, a suitable buffer system and other additives normally used for diagnostic means.

The finished test papers and test films can be used as such or glued in a known manner to support films or preferably sealed between plastic materials and fine-mesh networks, as described in the German Pat. No. 2,118,455 and brought into contact with the body fluid to be investigated (for example, blood, plasma, serum).

The invention is suitable for determining all antigens with at least two antigenic determinants. Examples of this are thyreotropin (TSH), carcinoembryonic antigen (CEA), hepatitis viruses (hepatitis B surface antigen, HBs), 1-alpha-fetoprotein (AFP), human chorionic gonadotropin (HCG), luteinizing hormone (LH), follicle-stimulating hormone (FHS), $\beta_2$-microglobulin, acid prostataphosphatase, prolactin, ferritin and insulin.

DETAILED DESCRIPTION OF PREFERRED EMBODIMENTS

Example 1

Preparation of Monoclonal Mouse IgG Aggregate by Cross Linking with a Homobifunctional Reagent Monoclonal antibody MAB33 IgG (>95% pure; sub-class composition K, $\gamma_1$; specificity anti(creatine kinase)) is isolated from ascites fluid by ammonium sulfate precipitation and chromatography on a DEAE ion exchanger (see A. Johnstone and R. Thorpe, Immunochemistry In Practice, Blackwell Scientific Publications 1982, pages 44–45).

IgG (50 mg) is dissolved in 3 mL of 0.025M bicarbonate/carbonate buffer at pH 9.5. Into this solution were pipetted 17 μL of 12.5% glutaric dialdehyde solution and the resulting mixture was incubated for 2 hours at 25° C. Subsequently, the solution was cooled in an ice bath and adjusted to a pH of 8.2 with 50 mM triethanoamine buffer. A freshly prepared sodium borohydride solution (0.6 mL of a solution of 8 mg sodium borohydride in 1 mL of doubly distilled water) was added to this solution and the resulting mixture was incubated for a further 2.5 hours at 0° C. Excess reagents were removed by dialysis for 16 hours at 0°–4° C. against 10 mM phosphate buffer at pH 7.5, containing 0.2M NaCl. The dialysate was concentrated by ultrafiltration to a volume of 1.25 mL. A portion of this concentrate (crude mixture) was used directly for suppressing the interference; 1.0 mL of this concentrate was chromatographed over a 2×40 cm gel filtration column packed with AcA22 (LKB); operating buffer: 10 mM phosphate/100 mM NaCl with a pH of 7.5. The eluate from the column was examined for protein content with a UV monitor at 280 nm and fractionated. The fractions of the total, protein-containing elution range were combined into 4 pools of equal volume. By calibrating the gel chromatography column with proteins of known molecular weight, it was possible to assign molecular weight ranges of 160,000 to 400,000, 400,000 to 1,000,000, 1,000,000 to 2,000,000 and 2,000,000 to 10,000,000 to the pools. After the pools were concentrated to a protein concentration of about 2 mg/mL, the IgG aggregate solutions of the different molecular weight ranges were used for suppressing interference.

Example 2

Preparation of Monoclonal Mouse IgG Aggregate by Cross Linking with Heterobifunction Reagent (a) Preparation of of MAB33-IgG-MH (Maleicimidohexanoyl-MAB33-IgG).

MAB33-IgG (100 mg) is dissolved in 4 mL of a 30 mM phosphate buffer of pH 7.1. To this solution were pipetted 20 μL (4 μmoles) of a 0.2M solution of maleicimidohexanoylsuccinimidate in dimethyl sulfoxide. The reaction mixture was incubated for 1 hour at 25° C. and then dialyzed for 16 hours at 0°–4° C. against 10 mM phosphate buffer having a pH of 6.1 and containing 50 mM of NaCl, 4.45 mL of solution with 22 mg of MAB33-IgG-MH/mL being obtained.

(b) Preparation of MAB33-IgG-SAMS (S-acetylmercaptosuccinyl MAB33-IgG)

MAB33-IgG (100 mg) was dissolved in 4 mL of 0.1M phosphate buffer of pH 8.0. To this solution were pipetted 40 μL of a 0.25M solution of S-acetyl-mercaptosuccinic anhydride in dimethyl sulfoxide. The reaction mixture is incubated for 1 hour at 25° C. and then dialyzed for 16 hours at 0°–4° C. against 10 mM phosphate buffer of pH 6.1 and containing 50 mM NaCl, 4.45 mL with 21.8 mg of MAB33-IgG-SAMS/mL being obtained.

(c) Cross Linking of MAB33-IgG-MH with MAB33-IgG-MS (Mercapto-succinyl-MAB33-IgG)

MAB33-IgG-SAMS (50 mg) was diluted to a concentration of 15 mg/mL in 25 mM phosphate buffer of pH 6.5 containing 2 mM of ethylenediaminetetraacetate (buffer A). To this solution were pipetted 75 μL of a 1M hydroxylamine solution and the resulting mixture was incubated for 20 minutes at 25° C.

Figure 1:
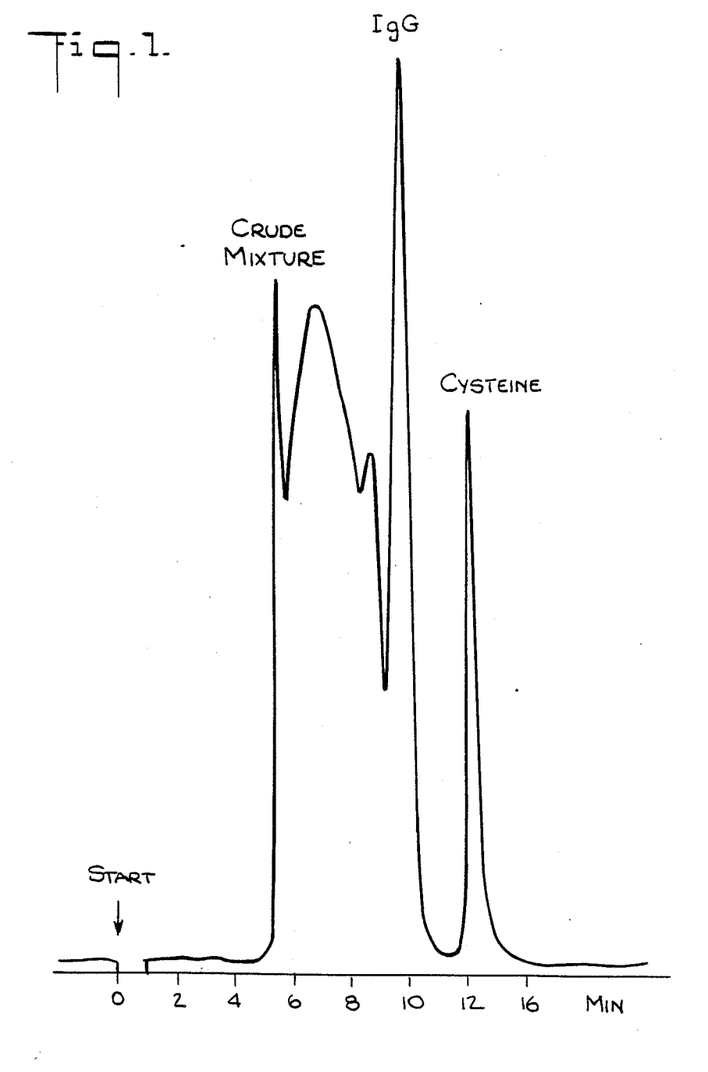
FIG. 1 shows the molecular weight distribution of aggregates of monoclonal antibody "MAB33".

This solution (3 mL) with 44 mg of MAB33-MS was diluted with buffer A to 6.0 mL and 4 mL of a solution with 88 mg of MAB33-IgG-MH was added to it. The mixture was incubated for 40 minutes at 25° C. and then mixed with cysteine to a concentration of 2 mM to terminate the cross linking reaction. After incubating for a further 30 minutes at 25° C., N-methylmaleicimide was added at a concentration of 5 mM and the temperature was maintained at 25° C. for a further hour. The reaction solution was dialyzed against 10 mM phosphate buffer (pH 7.5), containing 0.2M NaCl. The dialysate was concentrated by ultrafiltration to a protein concentration of 35 mg/mL and freed from a slight cloudiness by centrifugation. FIG. 1 shows a typical molecular weight distribution of such a dialysate (crude mixture) of an MAB33-IgG aggregate. The aggregate mixture can be used directly or after being divided into molecular weight fractions (AcA22 chromatography as in Example 1) for suppressing interference.

Example 3

Preparation of MAB33-IgG Aggregate Through Cross Linking by Way of Aminodextran (a) Preparation of S-Acetylthioacetyl Aminodextran Aminodextran (100 mg of Dextran T40, Pharmacia; 28 amino groups per molecular weight of 40,000) was dissolved in 4 mL of 30 mM phosphate buffer of pH 7.1. To this solution was pipetted 0.25 mL of a 0.2M S-acetylthioacetylsuccinimidate solution in dimethyl sulfoxide. The reaction mixture was incubated for 1 hour at 25° C. and then dialyzed against 10 mM phosphate buffer of pH 6.1, containing 50 mM NaCl. Yield: 90 mg of S-acetylthioacetylaminodextran in 4.5 mL of solution.

(b) Cross Linking of MAB33-IgG-MH with Thioacetyl-Amindextran

A solution (2 mL) of 20 mg/mL of S-acetylthioacetylaminodextran was adjusted to a pH of 6.5 with 0.1M NaOH, whereupon ethylenediaminetetraacetate was added to a concentration of 2 mM. To this solution was pipetted 40 μL of 1M hydroxylamine solution and the resulting mixture was incubated for 20 minutes at 25° C. Subsequently, the solution was diluted with 25 mM phosphate buffer of pH 6.5 to 6.8 mL and mixed with 7.2 mL of a solution of 158.4 mg MAB33-IgG-MH (prepared as in Example 2a). After incubating for 30 minutes at 25° C., cysteine was added to the reaction mixture up to a concentration of 2 mM and, after a further 30 minutes at 25° C. N-methylmaleicimide was added at a concentration of 5 mM and the temperature was maintained at 25° C. for a further hour. The polymer was dialyzed against 10 mM phosphate buffer of pH 7.5, containing 50 mM of NaCl. After centrifuging off a slight cloudiness, 19.5 mL of a solution of MAB33-

IgG-dextran aggregate was obtained with a protein content of 7.1 mg/mL.

Example 4

Preparation of MAB33-IgG Aggregate Through Cross Linking by Way of Bovine IgG (a) Preparation of Bovine-IgG-MH Polyclonal bovine IgG (100 mg) was reacted as in Example 2a) with 4 μmoles maleicimidohexanoylsuccinimidate. Yield: 4.45 mL of solution with 22 mg of bovine IgG-MH/mL.

(b) Preparation of MAB33-IgG-SATA (S-acetylthioacetyl-MAB33-IgG)

MAB33-IgG (100 mg) was dissolved in 4 mL of a 30 mM phosphate buffer with a pH of 7.1. To this solution were pipetted 20 μL (2 μmoles) of a 0.1M solution of S-acetylthioacetylsuccinimidate in dimethyl sulfoxide. The reaction mixture was incubated for 1 hour at 25° C. and then dialyzed for 16 hours at 0°-4° C. against 10 mM phosphate buffer, having a pH of 6.1 and containing 50 mM of sodium chloride. Yield: 4.45 mL of a solution with 22 mg MAB33-IgG-SATA/mL.

(c) Cross Linking of Thioacetyl-MAB33-IgG with Bovine-IgG-MH

MAB33-IgG-SATA (50 mg) was diluted with 25 mM phosphate buffer of pH 6.5 containing 2 mM ethylenediaminetetraacetate (buffer A), to a concentration of 15 mg/mL. To this solution were pipetted 75 μl of a 1M hydroxylamine solution and the mixture was incubated for 20 minutes at 25° C.

To 3 mL of this solution with 44 mg of thioacetyl-MAB33-IgG were added 4 mL of a solution with 88 mg of bovine IgG-MH and the mixture was incubated for 25 minutes at 25° C. The cross linking reaction was then terminated by adding cysteine up to a concentration of 2 mM and, after incubating for 30 minutes at 25° C., iodoacetamide up to a concentration of 5 mM. After incubating for a further hour at 25° C., the mixture was dialyzed for 16 hours at 0°-4° C. against 10 mM phosphate buffer of pH 7.5 containing 50 mM NaCl. After centrifuging the dialysate, 8.9 mL of MAB33-IgG-bovine-IgG aggregate with a protein concentration of 13 mg/mL were obtained.

Example 5

Preparation of MAB-IgG Aggregate Cross Linked with MAB33-Fab (a) Preparation of MAB33-Fab-SATA MAB33-IgG (200 mg) was split with papain into Fab/Fc and MAB33-Fab was isolated from the mixture by chromatography on DE52 cellulose (Whatman) (the method is described by A. Johnstone and R. Thorpe in Immunochemistry in Practice, Blackwell Scientific Publications 1982, 52-53). Yield: 95 mg of MAB33-Fab as salt-free lyophilisate.

MAB33-Fab (50 mg) was dissolved in 2 mL of 30 mM phosphate buffer of pH 7.1. To this solution was pipetted 30 μL (3 μmoles) of a 0.1M solution of S-acetylthioacetylsuccinimidate in dimethyl sulfoxide. The reaction mixture was incubated for 1 hour at 25° C. and then dialyzed for 16 hours at 0°-4° C. against 10 mM phosphate buffer of pH 6.1 containing 50 mM NaCl and 2 mM ethylenediaminetetracetate. A 2.6 mL solution with 18.5 mg of MAB33-Fab-SATA/mL was obtained.

(b) Cross Linking MAB33-IgG-MH with Thioacetyl-MAB33-Fab

MAB33-Fab-SATA (30 mg) was diluted with 25 mM phosphate buffer of pH 6.5 to a concentration of 15 mg/mL. To this solution was pipetted 50 μl of a 1M hydroxylamine solution and the mixture was incubated for 20 minutes at 25° C.

This solution (1.5 mL with 22 mg of thioacetyl-MAB33-Fab) was mixed with 55 mg of MAB33-IgG-MH (prepared as in 2a) and diluted with twice distilled water to a total volume of 10 mL. The mixture was incubated for 35 minutes at 25° C., after which the cross linking was terminated by the addition of cysteine up to a concentration of 2 mM. After 30 minutes at 25° C., N-methylmaleicimide was added up to a concentration of 5 mM and the mixture is incubated once more for 1 hour at 25° C. Subsequently, the reaction solution was dialyzed for 1 hour at 0°-4° C. against 10 mM phosphate buffer of pH 7.5, containing 0.1M NaCl. After centrifuging, 12.8 mL of a clear solution with 5.3 mg of MAB33-IgG-Fab aggregate/mL are obtained.

Example 6

Comparison of the Interference Suppression of Native MAB33-IgG and Different MAB33-IgG Aggregates in a CEA Enzyme Immunoassay with two Specific MAB reactants The reagents from an ENZYMUN® test package (Boehringer Mannheim GmbH) were used. The reagent tubes, contained in this test package, are coated with a monoclonal, CEA-specific mouse IgG (IgG1, K). The enzyme-labeled reactant is a monoclonal, CEA-specific mouse Fab peroxidase conjugate; the subclass composition of the Fab is K, $\gamma_1$).

The different MAB33-IgG preparations were added in increasing concentration to the incubation buffer and the test was carried out with human serum, in which strikingly effective interfering factors were detected. Table 1 shows the concentration of the MAB33-IgG preparation (in μg of protein/mL) in the incubation buffer, which suppresses the interference to such an extent, that the correct analyte content was found in the normal range (1-3.5 ng/mL).

Table 1

Relative Interference-Suppressing Function of Different MAB33 IgG Preparations

TABLE 1

Relative Interference-Suppressing Function of Different MAB33 IgG Preparations

| Addition to Incubation Buffer | μg/mL | Interference Suppression Factor | Absorbance | Apparent CEA Content in Serum P43 ng/mL |
|---|---|---|---|---|
| without | 0 | — | 1.636 | 58* |
| MAB33-IgG monomer | 9600 | 0.0026 | 0.132 | 3.4 |
| MAB33-IgG aggregate/GDA (crude mixture 1) | 34 | 0.74 | 0.126 | 3.1 |
| MAB33-IgG aggregate (crude mixture 2c) | 25 | 1 | 0.125 | 3.1 |
| MAB33-IgG dextran (3) | 43 | 0.58 | 0.129 | 3.3 |
| MAB33-IgG-bovine IgG aggregate (4) | 82 | 0.3 | 0.130 | 3.3 |
| MAB33-IgG-Fab aggregate (5) | 3 | 8.3 | 0.122 | 2.9 |

*This value lies outside of the range of the calibration curve as defined by the calibration points.

Example 7

Dependence of Interference-Suppressing Function on the Molecular Weight of the MAB33-IgG Aggregate The reagents and procedure for this experiment are described in Example 6. The MAB33-IgG preparations are prepared as described in Example 2.

Table 2

Interference Suppression of MAB33-IgG Aggregates as a Function of Molecular Weight

TABLE 2

Interference Suppression of Mab33-IgG Aggregates as a Function of Molecular Weight

| Addition to Incubation Buffer | Patient Serum No. 18[1] Absorbance | Patient Serum No. 18[1] ngCEA/mL[2] | Patient Serum No. 43[1] Absorbance | Patient Serum No. 43[1] ngCEA/mL[2] |
|---|---|---|---|---|
| without addition | 1.567 | 58[3] | 1.636 | 58[3] |
| 125 μg/mL monomeric MAB33-IgG | 0.148 | 3.9 | 1.703 | 58 |
| 10 μg/mL MAB33-IgG aggregate crude mixture | 0.115 | 2.7 | 0.179 | 6.2 |
| 30 μg/mL MAB33-IgG aggregate crude mixture | — | — | 0.125 | 3.1 |
| 5 μg/mL MAB33-IgG aggregate M.W. 2–10 million | 0.105 | 2.1 | 0.137 | 3.9 |
| 5 μg/mL MAB33-IgG aggregate M.W. 1–2 million | 0.109 | 2.4 | 0.285 | 11.0 |
| 5 μg/mL MAB33-IgG aggregate M.W. 400,000–1 million | 0.155 | 4.8 | 1.051 | 53.7 |
| 5 μg/mL MAB33-M.W. 160,000–400,000 | 0.364 | 16.3 | 1.239 | 58 |

1. The true content of CEA, determined with a reference method, lies in the range of 1–3.5 ng/mL.
2. Apparent CEA content, determined from the absorbance and the calibration curve with standard CEA samples according to the instructions for ENZYMUN CEA.
3. Outside of the calibration curve range as defined by the calibration points.

Example 8

Comparison of the Interference Suppression of MAB-IgG Aggregates, Produced from Different Monoclonal Antibodies Small test tubes from an ENZYMUN® package (Boehringer Mannheim GmbH), which were coated with a monoclonal anti-TSH mouse IgG (IgG1, K) were used. The remaining reagents were taken from the ENZYMUN CEA package as in Example 6. The test was conducted according to the instructions provided with this package. In conducting the test in this manner, a signal cannot be given by the analyte content of a serum sample, because the two specific reactants have different specificities. It is thus only a question of a model test, which gives a signal above the blank value with serum samples only when interfering factors are contained. The MAB-IgG aggregates, used for comparison, were prepared from MAB33 as in Example 2c or MS43.10.

Table 3

Comparison of IgG Aggregates of Different Monoclonal Antibodies in the Suppression of Interference of a Model Test

TABLE 3

Comparison of IgG Aggregates of Different Monoclonal Antibodies in the Suppression of Interference of a Model Test

| Addition to the Incubation Buffer | μg/L | Absorbance for Serum P43 |
|---|---|---|
| MAB33-IgG aggregate (2c) crude mixture | 0 | 0.900 |
| | 1.25 | 0.506 |
| | 2.5 | 0.366 |
| | 5 | 0.238 |
| | 10 | 0.195 |
| | 20 | 0.152 |
| MAB MS 43.10 Aggregate crude mixture | 0 | 0.900 |
| | 1.25 | 0.554 |
| | 2.5 | 0.406 |
| | 5 | 0.286 |
| | 10 | 0.202 |
| | 20 | 0.180 |

Absorbance for a serum sample without CEA and without interfering factor: 0.162.

Result: The suppression of interference by different monoclonal MAB-IgG aggregates is the same within the limits of accuracy of the test.

Example 9

Interference Suppression Effect of MAB33-IgG Aggregate and Monomeric MAB33-IgG in a Test With Biotinylated MAB-IgG Reactants In this test, two monoclonal hepatitis surface antigenic (HBsAG)-specific MAB-IgGs are used in biotinylated form (biotinylation was carried out by the method described by T. V. Updyke and G. L. Nicholson in Methods in Enzymology, 121 (1986) 717–725). One of these, MAB6E7-IgG, is one of the subtype IgG1/K, the other, MAB5A10-IgG, is of the subtype IgG2a, K. MAB5A10-Fab-POD conjugate was used as enzyme-labeled reactant.

Composition of the incubation buffer:
40 mM phosphate buffer of pH 7.0
0.2M sodium tartrate
0.5% (w/v) bovine serum albumin
0.1% (w/v) bovine IgG
0.5% (w/v) pluronic F68
0.01% (w/v) phenol
200 ng/mL MAB6E7-IgG (biotinylated)
25 ng/mL MAB6A10-IgG (biotinylated)
200 mU/mL MAB5A10-Fab-POD conjugate See Table 4 for addition of interference-suppressing protein.

Crude MAB33-IgG aggregate mixtures were prepared as described in Example 2c.

For the test, 0.2 mL of serum sample and 1 mL of incubation buffer were pipetted into a small polystyrene tube, which was coated with streptavidin. The tube was then incubated for 4 hours at room temperature. Subsequently, each tube was washed with 3×1.5 mL of tap water and 1 mL of substrate solution (ABTS/peroxide) from the ENZYMUN test package was added. After a further 1-hour incubation at room temperature, the absorbance in the reacted substrate solution was measured at 405 nm.

Table 4

Comparison of the Interference Suppression Effect of MAB33-IgG Preparations in a Sandwich Enzyme Immune Test with Biotinylated MAB-IgG Reactants

TABLE 4

Comparison of the Interference Suppression Effect of MAB33-IgG Preparations in a Sandwich Enzyme Immune Test with Biotinylated MAB-IgG Reactants

| Addition to the Incubation Buffer | μg/mL | Absorbance for Serum Sample | | |
|---|---|---|---|---|
| | | No. 100[1] | No. 489[1] | NS[2] |
| without | 0 | 1.390 | 0.262 | 0.042 |
| MAB33-IgG monomer | 1 | — | — | 0.042 |
| | 5 | 1.070 | 0.102 | 0.045 |
| | 10 | 0.884 | 0.068 | 0.048 |
| | 200 | 0.125 | 0.042 | 0.046 |
| | 400 | 0.080 | 0.048 | 0.049 |
| MAB-IgG Aggregate (2c) crude mixture | 0 | 1.044 | 0.378 | 0.047 |
| | 1 | 0.125 | 0.034 | 0.043 |
| | 5 | 0.043 | 0.045 | 0.048 |
| | 10 | 0.048 | 0.035 | 0.054 |

1: Serum samples Nos. 100 and 489 were obtained from a blood bank and were declared to be HBsAg free.
2: Serum of a healthy donor; the serum contained neither HBsAG nor interfering factor.

From the finding that, for sample No. 100, the same interference suppression to a signal of 0.125 is attained with 200 μg/mL of monomeric MAB33-IgG or 1 μg/mL of MAB33-IgG aggregate, it follows that IgG aggregate is 200 times as active in suppressing interference in this test.

Example 10

Interference Suppression Effect of MAB33-IgG Aggregate in a Test with a Dry Chemistry Reagent Carrier The determination with dry chemistry reagent carriers in a 1-step test according to the double antibody solid phase sandwich principle was carried out in rotor insert elements with a centrifugal analyzer with the analytical apparatus described in the DE-A 3425 008.5.

1. Preparation of the Reagent Solutions (a) Buffer I

Potassium phosphate buffer with a concentration of 50 mmoles/L and a pH of 6.0 was prepared by mixing 50 mmoles/L of $K_2HPO_4$ solution and 50 mmoles of $KH_2PO_4$ solution until a pH of 6.0 was reached.

(b) Buffer II

Buffer II is prepared in the same way as buffer I, with the difference that pH was adjusted to a value of 7.5 and that the buffer additionally contained 10 g/L bovine serum albumin and 150 mmoles of NaCl.

(c) Reactant $R_1$ Solution, Capable of Bonding with TSH

A monoclonal mouse anti-TSH antibody is used as reactant $R_1$. The ascites liquid containing this antibody is mixed with ammonium sulfate until the concentration of the latter is 1.8M. The precipitate is taken up in a buffer of 15 mM sodium phosphate of pH 7.0 and 50 mM sodium chloride. The solution, so obtained, is subjected to passage over DEAE cellulose. The antibody, which is capable of bonding TSH, was biotinylated (5 biotin/IgG) and was diluted with buffer II to a protein concentration of 1 mg/mL.

(d) Enzyme-Labeled Reactant $R_2$ Solution

A monoclonal mouse anti-TSH antibody was also used as reactant $R_2$. However, this antibody recognizes a different antigenic determinant than does reactant $R_1$. The ascites liquid, containing this antibody, was purified as described supra. The complete antibody was split by the method of R. R. Porter, Biochem. J. 73, (1959) page 119 to obtain the Fab fragments. The Fab fragments obtained are coupled with β-galactosidase by the method of Ishikawa, et al., J. of Immunoassay 4 (1983), pages 209–327. The reactant $R_2$ solution is diluted in buffer II to a concentration of 500 mU/mL (measured with o-nitrophenyl-β-galactoside at 37° C.).

(e) Interference Suppressing Protein

MAB33-IgG polymer, prepared as in Example 2, was dissolved in buffer II to a concentration of 1 mg/mL.

(f) Avidin Solution

Avidin was diluted with buffer I to a protein concentration of 50 μg/mL.

| (g) Substrate Solution | | |
|---|---|---|
| Chlorophenol red β-galactoside (prepared as in German OLS 3,345,748) | 5 mmoles/L | (3.05 g/L) |
| HEPES | 70 mmoles/L | (16.7 g/L) |
| NaCl | 154 mmoles/L | (9 g/L) |
| Bovine serum albumin | 0.3% | (3 g/L) |
| Tween 20 | 0.2% | (2 g/L) |
| pH (with NaOH) | 7.25 | |

2. Preparation of Reagent Carriers (a) Reagent Carrier 1 (without interference-suppressing protein)

A solution (40 μL), which contains 100 mmoles of sodium phosphate per liter at a pH of 7.3 (37° C.), 2 mmoles of magnesium chloride, 9 g of sodium chloride, 5 g of bovine serum albumin, 0.5 mg of biotinylated anti-TSH monoclonal antibody from the mouse (reactant $R_1$), 1,000 U anti-TSH-antibody-(mouse)-Fab-fragment-β-galactosidase conjugate (reactant $R_2$ solution) and the activity of which was determined with o-nitrophenyl-β-D-galactoside at 37° C., was added dropwise to a nonwoven material of commercial polyester paper. The material was subsequently dried at room temperature. Until it is used, this nonwoven material is kept at 4° C. and at a relative humidity of 20%.

(b) Reagent Carrier 1' (with interference-suppressing protein)

The preparation follows the same procedure as for reagent carrier 1, except that 0.01 g of MAB33-IgG aggregate from Example 2c (crude mixture) were contained per liter of impregnating solution.

(c) Reagent Carrier 2

Avidin (avidin solution) was fixed on a nonwoven cellulose material by the cyanogen-bromide activation method (German Pat. No. 1,768,512), 10 μg of avidin per gram of fiber material being offered for fixation. Uncoupled antibody was removed by washing and the nonwoven material is gently dried at room temperature. The nonwoven material, so obtained, was stored in the same way as reagent carrier 1.

3. Procedure for the Determination

The determination with the help of these two reagent carriers 1 and 2 or 1' and 2 took place in the apparatus described in the German Pat. No. 3,425,008.5 for carrying out analytical determinations.

This Patent Application teaches the use of a rotor insert element for automatic equipment for centrifugal analyses. The rotor insert element comprises a molded object that has a sample application chamber, which is connected with a plurality of reagent fields, which in each case contain an absorptive carrier material, which is impregnated with a particular reagent, at least one mixing valve chamber and one measuring chamber, which together form a sample liquid transport path, which leads from radially inwards to radially outwards when the insert element is fixed to the rotor, and furthermore at least one additional chamber leads to the measurement guide and is identical at least partly with the sample-liquid transport path.

Figure 2:
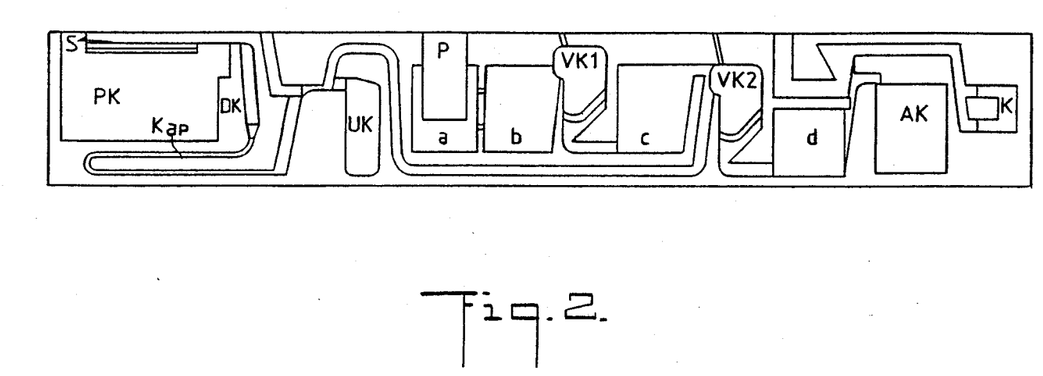
FIG. 2 depicts a device of the type which may be used in the assays described herein.

Moreover, the sample-liquid transport path leads from one sample application chamber (P), over a chamber (a) filled with absorptive material and containing a buffer, a chamber (c) and a first valve chamber (VK1), which is disposed between chambers (a) and (c), to a second valve chamber (VK2) and from this over chamber (d) and over a collection chamber (AK) to the measurement chamber (K). To accommodate a further liquid, a substrate chamber (PK), constructed as a pump chamber having an entry port (S), is provided, which is connected over a metering device, consisting of a metering chamber (DK) and a capillary (Kap), and an overflow chamber (UK) with the second valve chamber (VK2) (see FIG. 2). An additional chamber (b) is shown, which is not utilized in the assays described herein, but is available if necessary.

Reagent carrier 1 and reagent carrier 2 are used to determine the extinction a (measurement signal including the interfering signal) and reagent carriers 1' and 2 are used to determine the extinction b (specific measurement signal without interfering signal).

Reagent carrier 1 or 1' is placed on field c of the rotor insert element and reagent carrier 2 is placed on field d. At the same time, 40 μL of concentrated sample are pipetted through an opening at the upper edge directly onto field a and 270 μL of substrate solution are pipetted into chamber PK. Through a suitable centrifugation program, in which high rotational speeds alternate with a zero rotational speed, the sample and the substrate solution are then conveyed in the direction of the separating matrix and the cuvette.

In the course of the program, reactants $R_1$ and $R_2$, with or without the interference-suppressing protein, are eluted by the sample liquid from field c and the homogeneous mixture is subsequently caused to react. The complexes formed are bound over $R_1$ to avidin on field d. The transfer of sample from field c to field d takes place within a very short time.

The substrate solution is divided by the metering chamber DK into portions, of which the first are used to wash out excess conjugate, which has not been complexed.

Interfering factors, which could cross link $R_2$, are neutralized by the use of 10 μg interference-suppressing protein/mL of test solution and also washed out (use of reagent carrier 1').

The β-galactosidase activity, bound through complex formation to d, is proportional to the amount of TSH contained in the sample or to the sample blank. This activity is determined with a further substrate portion, the substrate being converted in a 5-minute reaction to colored products. The color formed and the further development of color per minute in the liquid phase are measured in the cuvette at 576 nm. The follwing results were obtained under these conditions:

Table 5

TABLE 5

| Sample | a | | b | |
|---|---|---|---|---|
| | Abs. [mE] | Conc. [uU/mL] | Abs. [mE] | Conc. [uU/mL] |
| TSH calibrator 0 uU/mL[c] | 451 | 0 | 457 | 0 |
| TSH calibrator 19.6 uU/mL[c] | 3331 | 19.6 | 3311 | 19.5 |
| Human serum I | 669 | 1.5 | 725 | 1.8 |
| Human serum 43 with interfering factors | 6790 | 38 | 662 | 1.5 |

All measurements were carried out at a wavelength of 576 nm and a layer thickness of 0.3 cm and recalculated to a layer thickness of 1 cm.

(a) TSH determined using reagent carrier 1
(b) TSH determined using reagent carrier 1' with MAB33-IgG polymer to neutralize M-Fab-specific interfering factors
(c) TSH standard calibrated on 2nd IRP 80/588.

The TSH content in human serum 43 was confirmed with an ENZYMUN TSH Test of the Boehringer Company to be 1.4 uU/mL. As specific reactants, this test contains a tube coated with MAB-anti-TSH and a polyclonal sheep anti-TSH-Fab-POD conjugate. The latter is inert towards interfering factors in HS 43.

It will be understood that the specification and examples are illustrative but not limitative of the present invention and that other embodiments within the spirit and scope of the invention will suggest themselves to those skilled in the art.

We claim:

1. Method for determining a compound of a sample of a biological fluid obtained from a first animal species, which biological fluid contains an interferent, comprising contacting said sample with at least two immunoreactants obtained from an animal species different from said first animal species, wherein said immunoreactants specifically bind with said component to be determined and further contacting said sample with a soluble substance which prevents said interferent from interfering with binding between said component to be determined and said at least two immunoreactants, said substance characterized as a cross-linked immunoaggregate containing an immunocomponent obtained from an animal species different from said first animal species, at a concentration from about 0.1 to about 50 ug/ml, wherein said substance does not bind with said component to be determined, said contacting taking place under conditions favoring formation of an identifiable complex between said component to be determined and said immunoreactants, and determining said complex or non-complexed immunoreactant as a measure of said component to be determined.

2. Method of claim 1, wherein said immunoaggregate is derived from a polyclonal antibody.

3. Method of claim 1, wherein said immunoaggregate is derived from a monoclonal antibody.

4. Method of claim 1, wherein said immunoreactants are antibodies or fragments thereof.

5. Method of claim 1, wherein at least one of said immunoreactants is a Fab fragment.

6. Method of claim 1, wherein at least one of said immunoreactants is a F(ab')$_2$ fragment.

7. Method of claim 1, wherein said immunoaggregate is aggregated nonspecific IgG.

8. Method of claim 7, wherein said immunoaggregate is added at a concentration of from about 5 to about 25 µg/ml.

9. Method of claim 7, wherein said immunoaggregate is added at a concentration of from about 5 to about 10 µg/ml.

10. Method of claim 1, wherein said immunoaggregate comprises nonspecific IgG cross-linked to a second macromolecule wherein said second macromolecule is water soluble.

11. Method of claim 10, wherein said second macromolecule is a Fab or F(ab')$_2$ fragment, said nonspecific IgG and said second macromolecule being derived from the same species and subtype as at least one of said immunoreactants.

12. Method of claim 10, wherein said second macromolecule is an Fc free IgG fragment obtained from a species different from said aggregated IgG species and from said sample species.

13. Method of claim 10, wherein said second macromolecule is a water soluble protein.

14. Method of claim 10, wherein said second macromolecule is a water soluble polysaccharide.

15. Method of claim 10, wherein said second macromolecule is a water soluble polymer.

16. Method of claim 1, wherein said immunoaggregate is characterized by a molecular weight of at least about 320,000 daltons.

17. Method of claim 1, wherein said immunoaggregate is characterized by a molecular weight of from about 320,000 to about 10 million daltons.

18. Method of claim 1, wherein said immunoaggregate is an immunoaggregate produced by heat treatment.

19. Method of claim 1, wherein said immunoaggregate is an immunoaggregate produced by chemical crosslinking.

20. Method of claim 1, wherein at least one of said immunoreactants carries a label.

21. Method of claim 1, wherein at least one of said immunoreactants is fixed to a matrix.

22. Method of claim 1, wherein at least one of said immunoreactants is biotinylated.

23. Reagent for determining a component in a sample of a body fluid obtained from a first animal species, comprising at least two immunoreactants which specifically bind to said component to be determined wherein said immunoreactants are derived from an animal species different from said first animal species and a soluble substance which prevents interference with binding of said immunoreactants and said component to be determined by an interferent in said body fluid sample, said substance characterized as a cross-linked immunoaggregate containing an immunocomponent obtained from an animal species different from said first animal species, said immunoaggregate being further characterized by a molecular weight of at least 320,000 daltons, wherein said substance does not bind with said component to be determined, said substance being present in a concentration of from about 0.1 to about 50 ug/ml, and a buffer.

24. Reagent of claim 23, wherein said immunocomponent is a polyclonal antibody, a monoclonal antibody, or a fragment thereof.

25. Reagent of claim 23, wherein at least one of said immunoreactants is an antibody or a fragment thereof.

26. Reagent of claim 23, wherein at least one of said immunoreactants is a Fab or F(ab')$_2$ fragment.

27. Reagent of claim 23, wherein said immunoaggregate comprises IgG.

28. Reagent of claim 23, wherein said immunoaggregate comprises IgG cross-linked to a secon water soluble macromoleucle.

29. Reagent of claim 23, wherein said immunoaggregate comprises IgG from two different species.

30. Reagent of claim 28, wherein said second macromolecule is an Fc free IgG fragment.

31. Reagent of claim 28, wherein said second macromolecule is a water soluble protein.

32. Reagent of claim 28, wherein said second macromolecule is a water soluble polysaccharide.

33. Reagent of claim 28, wherein said second macromolecule is a water soluble polymer.

34. Reagent of claim 23, wherein at least one of said immunoreactants is a Fab fragment.

35. Reagent of claim 23, wherein at least one of said immunoreactants is a F(ab')$_2$ fragment.

36. Reagent of claim 23, wherein at least one of said immunoreactants is an Fc containing IgG.

37. Reagent of claim 28, wherein said immunoaggregate is selected from the group consisting of an aggregate of IgG, an aggregate of IgG and Fab, and an aggregate of IgG and F(ab')$_2$.

38. Reagent of claim 37, wherein said IgG and said Fab or F(ab')$_2$ are obtained from the same species as at least one of said immunoreactants.

39. Reagent of claim 38, wherein said IgG and said Fab or F(ab')$_2$ are obtained from the same subtype as at least one of said immunoreactants.

40. Reagent of claim 37, wherein said IgG is a monoclonal antibody and said Fab or F(ab')$_2$ are obtained from a monoclonal antibody.

41. Reagent of claim 23, further comprising at least one member selected from the group consisting of a reaction accelerator, a detergent, and a stabilizer.

* * * * *